(12) United States Patent
Tomii et al.

(10) Patent No.: US 10,513,798 B2
(45) Date of Patent: Dec. 24, 2019

(54) METHOD FOR DETERMINING DEFECT REGION

(71) Applicant: SHIN-ETSU HANDOTAI CO., LTD., Tokyo (JP)

(72) Inventors: Kazuya Tomii, Shirakawa (JP); Hiroyasu Kikuchi, Nishigo-mura (JP)

(73) Assignee: SHIN-ETSU HANDOTAI CO., LTD., Tokyo (JP)

( * ) Notice: Subject to any disclaimer, the term of this patent is extended or adjusted under 35 U.S.C. 154(b) by 92 days.

(21) Appl. No.: 15/770,333

(22) PCT Filed: Oct. 24, 2016

(86) PCT No.: PCT/JP2016/004664
§ 371 (c)(1),
(2) Date: Apr. 23, 2018

(87) PCT Pub. No.: WO2017/085903
PCT Pub. Date: May 26, 2017

(65) Prior Publication Data
US 2018/0312994 A1 Nov. 1, 2018

(30) Foreign Application Priority Data
Nov. 17, 2015 (JP) .................. 2015-224369

(51) Int. Cl.
*C30B 33/00* (2006.01)
*C30B 29/06* (2006.01)
(Continued)

(52) U.S. Cl.
CPC .............. *C30B 29/06* (2013.01); *C30B 15/14* (2013.01); *G01B 11/30* (2013.01); *G01N 1/32* (2013.01); *G01N 21/956* (2013.01)

(58) Field of Classification Search
CPC .......... C30B 29/06; C30B 33/00; C30B 15/20
See application file for complete search history.

(56) References Cited

U.S. PATENT DOCUMENTS 5,968,264 A 10/1999 Iida et al.
6,159,438 A 12/2000 Iida et al.
(Continued)

FOREIGN PATENT DOCUMENTS

JP H10-297995 A 11/1998
JP H11-079889 A 3/1999
(Continued)

OTHER PUBLICATIONS

May 22, 2018 International Preliminary Report on Patentability issued in International Patent Application No. PCT/JP2016/004664.
(Continued)

*Primary Examiner* — Robert M Kunemund
(74) *Attorney, Agent, or Firm* — Oliff PLC

(57) ABSTRACT

A method for determining a defect region of a silicon wafer which is sliced off from a silicon single crystal manufactured by a CZ method, the method including: (1) mirror-surface processing the silicon wafer in such a manner that a haze level of a surface thereof in haze measurement performed by a particle counter which uses a laser having a wavelength of 266 nm becomes 0.06 ppm or less; (2) measuring the number of defects and/or a defect density distribution on the mirror-surface-processed surface of the silicon wafer by using a particle counter capable of measuring defects having a size of 15 nm or less; and (3) determining the defect region of the silicon wafer from the measured number of the defects and/or defect density distribution.

8 Claims, 3 Drawing Sheets

(51) Int. Cl.
*C30B 15/14* (2006.01)
*G01N 21/956* (2006.01)
*G01B 11/30* (2006.01)
*G01N 1/32* (2006.01)

(56) References Cited

U.S. PATENT DOCUMENTS

| | | | |
|---|---|---|---|
| 6,743,495 B2* | 6/2004 | Vasat | C30B 29/06 117/3 |
| 6,995,077 B2* | 2/2006 | Siebert | B82Y 15/00 438/478 |
| 2002/0174828 A1* | 11/2002 | Vasat | C30B 29/06 117/90 |
| 2014/0327112 A1 | 11/2014 | Libbert et al. | |

FOREIGN PATENT DOCUMENTS

| | | |
|---|---|---|
| JP | 2000-058509 A | 2/2000 |
| JP | 2000-269288 A | 9/2000 |
| JP | 2003-142544 A | 5/2003 |
| JP | 2004-153083 A | 5/2004 |
| JP | 2006-112871 A | 4/2006 |
| JP | 2008-222505 A | 9/2008 |
| JP | 2009-021572 A | 1/2009 |
| JP | 2015-501533 A | 1/2015 |

OTHER PUBLICATIONS

Jan. 17, 2017 International Search Report issued in International Patent Application No. PCT/JP2016/004664.

* cited by examiner (A-A)  (B-B)  (C-C)

(i)  (ii)  (iii)

(i)  (ii)  (iii)

(i)　　　　　　　(ii)　　　　　　　(iii)

METHOD FOR DETERMINING DEFECT REGION

TECHNICAL FIELD

The present invention relates to a method for determining a defect region of a silicon wafer sliced off from a silicon single crystal, which is manufactured by a CZ method, with the use of a particle counter.

BACKGROUND ART

In silicon single crystals manufactured by a Czochralski (CZ) method, there are defects called grow-in defects such as an FPD (Flow Pattern Defect), an LSTD (Laser Scattering Tomography Defect), a COP (Crystal Originated Particle), and the like, they can be a factor which degrades device characteristics, and hence importance is given to a reduction in these defects.

With the aim of describing these defects, a description will be first given as to generally known facts about a vacancy type point defect called vacancy (which will be referred to as V hereinafter) and an interstitial type silicon point defect called interstitial-Si (which will be referred to as I hereinafter) which are taken into a silicon single crystal.

In a silicon single crystal, a V region means a region which has many concave portions or hole-like portions which are produced due to insufficiency of silicon atoms, and an I region means a region which has many dislocations or lumps of superfluous silicon atoms produced when silicon atoms are superfluously present. In particular, it is known that the grown-in defects such as FPDs, LSTDs, and COPs produced in the V region are a factor which degrades oxide dielectric breakdown voltage characteristics in a device process. Further, a neutral region (which will be referred to as an N region hereinafter) which has no (less) insufficiency or superfluousness of atoms is present between the V region and the I region. Furthermore, it is known that the grown-in defects (FPDs, LSTDs, COPs, and the like) are produced consistently when V or I is supersaturated, and that no grown-in defect is present when atoms are saturated or less even though the atoms are slightly biased.

Moreover, it has been confirmed that defects called OSFs (Oxidation Induced Stacking Faults) are distributed in a ring-like form near a boundary between the V region and the I region when seen in a cross section vertical to a crystal growth axis (a region where OSFs are produced will be referred to as an "OSF region" hereinafter). Additionally, it is known that these defect regions change depending on, e.g., a pulling rate at the time of growing a crystal.

As a method for evaluating the grown-in defects, a method which uses a heat treatment or an oxidation treatment like Patent Literature 1 or Patent Literature 2 or a method which uses etching like Patent Literature 3 is general. Further, as a method for determining a defect region, especially the N region, a method for performing the oxidation treatment like Patent Literature 4 is known, and a method combined with a Cu deposition method is also known.

Furthermore, like Patent Literature 5, a method for manufacturing a silicon single crystal having a desired defect region like a V region or an N region by adjusting manufacturing conditions such as an in-furnace temperature at the time of manufacturing a single crystal has been also suggested, but the manufacturing conditions required for the N region are particularly difficult, and stable products are hardly provided. Thus, even in case of manufacturing a single crystal by such a method, determining a defect region as a quality inspection is important.

CITATION LIST

Patent literatures

Patent Literature 1: Japanese Unexamined Patent Publication (Kokai) No. Hei 10-297995
Patent Literature 2: Japanese Unexamined Patent Publication (Kokai) No. 2000-269288
Patent Literature 3: Japanese Unexamined Patent Publication (Kokai) No. 2000-058509
Patent Literature 4: Japanese Unexamined Patent Publication (Kokai) No. 2004-153083
Patent Literature 5: Japanese Unexamined Patent Publication (Kokai) No. Hei 11-79889

DISCLOSURE OF INVENTION

Problem to be Solved by the Invention

In case of determining each defect region (the V region, the OSF region, and the N region) of wafers sliced off from an ingot, it is general to perform, e.g., a heat treatment as Patent Literatures 1 to 4, and then conduct an OSF inspection or an oxide dielectric breakdown voltage evaluation, a wafer lifetime inspection, or the like. However, according to these methods, the heat treatment alone needs approximately 20 hours, and a full day is required at the shortest until a determination including the subsequent OSF inspection and the like is made. Moreover, since these inspections are destructive inspections, they can be a factor which degrades a product yield.

In view of the problem, it is an object of the present invention to provide a method for determining a defect region of a silicon wafer, which is sliced off from a silicon single crystal manufactured by a CZ method, in a short time by a nondestructive inspection.

Means for Solving Problem

To achieve the object, the present invention provides method for determining a defect region of a silicon wafer which is sliced off from a silicon single crystal manufactured by a CZ method, comprising:

(1) mirror-surface processing the silicon wafer in such a manner that a haze level of a surface thereof in haze measurement performed by a particle counter which uses a laser having a wavelength of 266 nm becomes 0.06 ppm or less;

(2) measuring the number of defects and/or a defect density distribution on the mirror-surface-processed surface of the silicon wafer by using a particle counter capable of measuring defects having a size of 15 nm or less; and (3) determining the defect region of the silicon wafer from the measured number of the defects and/or defect density distribution.

According to such a method, when the haze level of the silicon wafer whose defect region is to be determined is set to a predetermined value or less and the particle counter having a predetermined detection accuracy is used, each crystal defect can be sensitively detected, and the defect region of the silicon wafer can be determined from the measured number of the defects and/or the defect density distribution in a short time by a nondestructive inspection.

Additionally, it is preferable that a V region, an OSF region, and an N region are determined as the defect region.

The method for determining a defect region according to the present invention is particularly effective for a determination of the V region, the OSF region, and the N region.

Further, it is preferable that, before (3) by the particle counter used in (2), the number of defects and/or a defect density distribution on a surface of a silicon wafer which has the same oxygen concentration as that of the silicon wafer and has an already identified defect region are measured and a correspondence relation between the defect region and the number of the defects and/or the defect density distribution on the surface of the silicon wafer is obtained in advance, and, in (3), the defect region of the silicon wafer is determined from the number of defects and/or the defect density distribution measured in (2) based on the correspondence relation obtained in advance.

When the correspondence relation between the defect region and the number of the defects and/or the defect density distribution on the silicon wafer surface is obtained in advance in this manner, the defect region of the silicon wafer can be determined in a shorter time.

Furthermore, it is preferable that the silicon wafer has oxygen concentration of 5 to 20 ppma (JEIDA).

When such oxygen concentration is provided, a difference in number of defects or defect density distribution between defect regions becomes more clear, and hence the defect region of the silicon wafer can be further accurately determined.

Effect of the Invention

As described above, according to the method for determining a defect region of the present invention, in each silicon wafer sliced off from a silicon single crystal manufactured by the CZ method, defect regions, e.g., the V region, the OSF region, and the N region can be accurately determined, and a time required for the determination can be greatly reduced. Moreover, according to the method for a determining a defect region of the present invention, since this determination is conducted by the nondestructive inspection with the use of a particle counter, a reduction in product yield can be avoided.

BEST MODE(S) FOR CARRYING OUT THE INVENTION

As described above, there has been demanded development of a method for determining each defect region of a silicon wafer sliced off from a silicon single crystal manufactured by the CZ method in a short time by a nondestructive inspection.

As a result of repeatedly conducting the earnest examination of the object, the present inventors have found out that the object can be achieved by setting a haze level of a silicon wafer whose defect region is to be determined to a predetermined value or less, measuring crystal defects by using a particle counter having a predetermined detection accuracy, and determining the defect region from this result, thereby bringing the present invention to completion.

That is, the present invention is a method for determining a defect region of a silicon wafer which is sliced off from a silicon single crystal manufactured by a CZ method, the method including: (1) mirror-surface processing the silicon wafer in such a manner that a haze level of a surface thereof in haze measurement performed by a particle counter which uses a laser having a wavelength of 266 nm becomes 0.06 ppm or less; (2) measuring the number of defects and/or a defect density distribution on the mirror-surface-processed surface of the silicon wafer by using a particle counter capable of measuring defects having a size of 15 nm or less; and (3) determining the defect region of the silicon wafer from the measured number of the defects and/or defect density distribution.

It is to be noted that the particle counter will now be briefly described. The particle counter generally includes an incidence system and a detection system, irradiates a silicon wafer with incident light, and detects each defect present on a surface of this silicon wafer as an LPD (Light Point defect) from intensity of scattered light. It is known that, when the particle counter counts the number of the LPDs, roughness which is present on the wafer surface and is approximately several to tens of nm becomes an obstruction factor. The roughness of approximately several to tens of nm is a haze. Usually, intensity of scattered light caused by the haze is expressed by a ratio to intensity of incident light and, for example, when the intensity of the scattered light is one millionth of the incident light intensity 1, the intensity of the scattered light (i.e., a haze level) is expressed as 1 ppm.

The invention will now be described hereinafter in detail with reference to the drawings, but the present invention is not restricted thereto.

Figure 1:
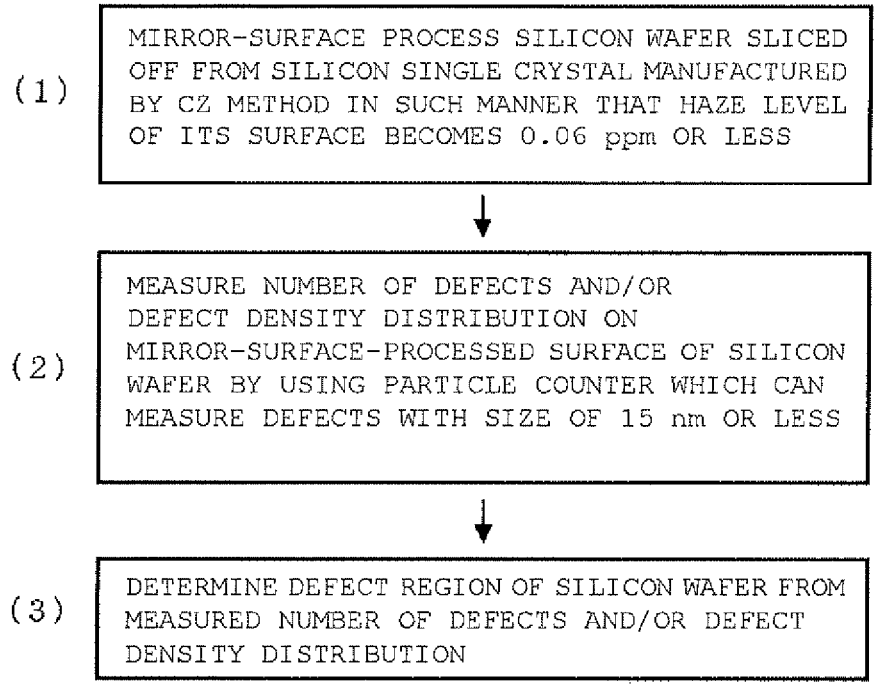
FIG. 1 is a flowchart showing an example of a method for determining a defect region according to the present invention.

FIG. 1 is a flowchart showing an example of the method for determining a defect region according to the present invention. In the method for determining a defect region in FIG. 1, each defect region is determined by the following processes (1) to (3).

(1) Mirror-surface processing a silicon wafer sliced off from a silicon single crystal manufactured by the CZ method in such a manner that its surface has a haze level of 0.06 ppm or less.

(2) Measuring the number of defects and/or a defect density distribution on the mirror-surface-processed silicon wafer surface by using a particle counter which can measure defects having a size of 15 nm or less.

(3) Determining each defect region of the silicon wafer from the measured number of defects and/or defect density distribution.

Each process will now be described hereinafter in more detail.

[Process (1)]

In the process (1), a silicon wafer sliced off from a silicon single crystal manufactured by the CZ method is mirror-surface processed in such a manner that its surface has a haze level of 0.06 ppm or less. It is to be noted that a smaller haze level is preferable.

As a previous step of the process (1), the silicon wafer which is to be subjected to a defect region determination is sliced off from the silicon single crystal manufactured by the CZ method (slicing). Then, before the mirror-surface processing, chamfering, lapping/surface grinding/double head grinding, etching, and the like may be performed. It is to be noted that these processes can be carried out by a well-known method.

Subsequently, the thus prepared silicon wafer is mirror-surface processed. The mirror-surface processing is constituted of polishing and cleaning, and flatness of the silicon wafer subjected to the etching or the like as described above is further improved and a surface of the silicon wafer is made into a mirror surface in the polishing. It is to be noted that the "flatness" described here has various frequency components, and it includes Warp (warpage) or waviness of large wavelength, roughness of small wavelength, micro roughness, a haze, and the like.

Frequency components concerning the haze can be reduced by adjusting a polishing agent, a polishing pad, a polishing temperature, and the like used in the polishing. More specifically, for example, it is preferable to set an average particle diameter of silica contained in the polishing agent to 30 nm or less, provide a nap layer having many elongated small holes (naps) formed therein to the polishing pad, and finish the nap layer to be soft by using an ether-based resin or the like, but the present invention is not restricted thereto.

In the cleaning after the polishing, a polishing liquid or the polishing agent used in the polishing is removed from the silicon wafer, and metal impurities adhering to the silicon wafer surface layer or particles caused by an environment are removed.

It is to be noted that, in the cleaning, preventing degradation of haze quality on the silicon wafer surface made in the polishing is important, and the cleaning can be performed without degrading the haze quality by adjusting, e.g., a cleaning liquid or a cleaning temperature. More specifically, for example, as the cleaning, it is preferable to perform cleaning using a hydrofluoric acid and ozone after general cleaning using SC1 and set an etching removal of the silicon wafer to 0.1 to 2.0 nm, but the present invention is not restricted thereto.

As the polishing conditions, cleaning conditions, and the like, any conditions which are well known in conventional examples can be adopted as long as they are conditions which enable setting the haze level to 0.06 ppm or less in the haze measurement based on the particle counter using a laser having a wavelength of 266 nm.

Then, the haze level of the mirror-surface-processed silicon wafer surface is measured. At this time, in the present invention, haze measurement adopting the particle counter which uses the laser with the wavelength of 266 nm is performed. As an apparatus which can be used for such haze measurement, for example, there is a DWO mode of SurfScan SP3 manufactured by KLA-Tencor Corporation. It is to be noted that a haze detection accuracy differs depending on a wavelength of the laser, and hence attention must be paid to the point that a value of the haze changes when a particle counter adopting the laser with a different wavelength is used.

In the present invention, the mirror-surface processing is performed in such a manner that the haze level of the mirror-surface-processed silicon wafer surface measured as described above becomes 0.06 ppm or less. That is, when the measured haze level exceeds 0.06 ppm, the silicon wafer whose mirror-surface-processed surface has the haze level of 0.06 ppm or less is prepared by again mirror-surface processing the same wafer or by newly mirror-surface processing another wafer.

[Process (2)]

In the process (2), the particle counter which can measure defects having a size of 15 nm or less is used to measure the number of defects and/or a defect density distribution on the silicon wafer surface mirror-surface processed in the process (1).

With using the particle counter, crystal defects present on the silicon wafer surface can be detected as LPDs as described above, and counting the number of the LPDs enables measuring the number of defects and/or the defect density distribution on the silicon wafer surface.

It is to be noted that, in the present invention, the particle counter which can measure defects having a size of 15 nm or less is used. When a particle counter having a lower detection accuracy (e.g., one which can detect defects having a size of not less than approximately 20 nm) is used, a difference in number of defects or in defect density distribution between respective defect regions (the OSF region and the N region in particular) becomes unclear, and hence these regions cannot be discriminated from each other. It is to be noted that, as the particle counter which can measure defects having a size of 15 nm or less, for example, there is SurfScan SP5 manufactured by KLA-Tencor Corporation.

[Process (3)]

In the process (3), each defect region of the silicon wafer is determined from the number of the defects and/or the defect density distribution measured in the process (2). It is to be noted that the method for determining a defect region according to the present invention is particularly effective for a determination of the V region, the OSF region, and the N region.

Figure 2:
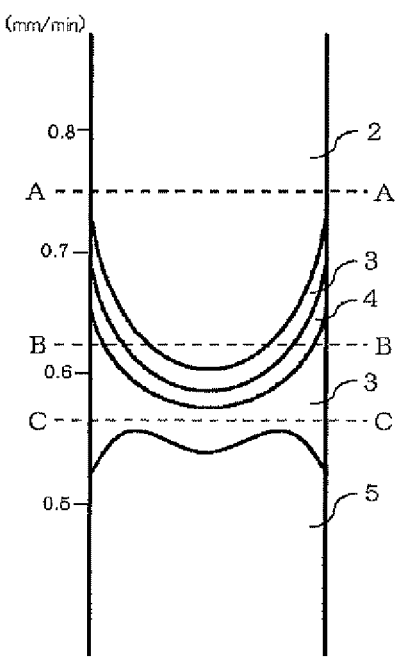
FIG. 2 is a schematic view showing each defect region in a silicon single crystal grown by the CZ method while reducing a pulling rate.

Here, characteristics of each defect region and a map will now be described. FIG. 2 is a schematic view showing each defect region in a silicon single crystal grown by the CZ method while reducing a pulling rate. As shown in FIG. 2, in the silicon single crystal 1 grown by the CZ method while reducing the pulling rate, there are a V region 2, an N region 3, an OSF region 4, and an I region 5. Characteristics of each of these defect regions are as described above. Further, A-A, B-B, and C-C in FIG. 2 indicate positions at which silicon wafers including the respective defect regions are sliced off from the silicon single crystal 1, and FIG. 3 schematically shows defect density distributions within surfaces of silicon wafers sliced off at the positions A-A, B-B, and C-C in FIG. 2.

Figure 3:
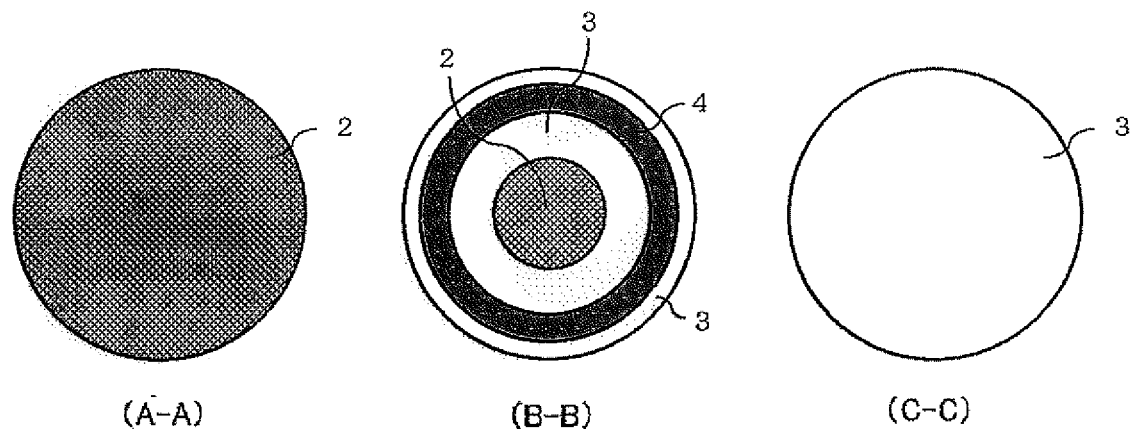
FIG. 3 is wafer maps schematically showing defects within silicon wafer planes cut along A-A, B-B, and C-C in the silicon single crystal in FIG. 2.

As shown in FIG. 3, in a silicon wafer, which was sliced off from the position A-A, whose defect region is the V region in its entire plane, grown-in defects such as FPDs, LSTD, or COP are produced on the entire silicon wafer plane. Furthermore, in a silicon wafer, which was sliced off at the position B-B, includes the V region, the N region, and the OSF region, a ring-like defect (OSF ring) which is revealed by a thermal oxidation treatment are produced, and grown-in defects represented by the V region are produced in a central portion. On the other hand, in a silicon wafer, which was sliced off at the position C-C, whose defect region is the N region in its entire plane, defects are quite hardly produced even though a heat treatment or the like is performed. In this manner, essentially, since each defect region has a different number of defects or defect density distribution, it can be considered that, when defect detection sensitivity of the particle counter can be enhanced, each defect region of the silicon wafer can be determined from the number of defects and/or the defect density distribution measured by the particle counter even though etching, a heat treatment, or the like is not performed.

Thus, before the process (3), the number of defects and/or a defect density distribution on a surface of another silicon wafer which has the same oxygen concentration as that of a silicon wafer of a defect region determination target and has already identified defect regions is measured by a particle counter which is used in the process (2), a correspondence relation between the defect regions and the number of defects and/or the defect density distribution on the silicon wafer surface is obtained in advance, and, in the process (3), the defect regions of the silicon wafer can be determined from the number of the defects and/or the defect density distribution measured in the process (2) based on the correspondence relation obtained in advance. When the correspondence relation between the defect regions and the number of the defects and/or the defect density distribution on the silicon wafer surface is obtained in advance in this manner, the defect regions of the silicon wafer can be determined in a shorter time.

Moreover, in the present invention, as the silicon wafer whose defect regions are to be determined, it is preferable to use a silicon wafer having oxygen concentration (initial oxygen concentration) of 5 to 20 ppma (JEIDA). That is because the number of defects measured by the particle counters relates to the oxygen concentration of the silicon wafer. When the oxygen concentration is 5 ppma or more, since the number of defects in the V region and the OSF region increases, a difference in the number of defects or defect density distribution between the V region, the OSF region, and the N region becomes more clear, and the defect regions can be more accurately determined only from a result of the measurement of the number of the defects and/or the defect density distribution performed by the particle counter (i.e., without carrying out a determination based on the correspondence relation obtained in advance as described above). When the oxygen concentration is 8 ppma or more, a difference between the defect regions becomes more clear, which is further preferable. Additionally, when the oxygen concentration is 20 ppma or less, there is no fear that the number of the defects provided by the particle counter overflows in the measurement of the V region, which is preferable.

As described above, according to a method for determining a defect region of the present invention, in each silicon wafer sliced off from a silicon single crystal manufactured by the CZ method, defect regions such as a V region, an OSF region, and a N region can be accurately determined, and a time required for the determination can be greatly reduced. Further, according to the method for determining a defect region of the present invention, since this determination is made with the use of the particle counter by a nondestructive inspection, a product yield can be prevented from being lowered.

EXAMPLES

The present invention will now be more specifically described hereinafter with reference to an example and comparative examples, but the present invention is not restricted thereto.

In Example 1 and Comparative Examples 1 and 2, silicon wafers with already identified defect regions sliced off from the same silicon single crystal were used. It is to be noted that a silicon single crystal with a diameter of 300 mm and initial oxygen concentration of 11 ppma (JEIDA) grown by the CZ method while changing a pulling rate was used. Further, as the silicon wafers, three types of silicon wafers, i.e., (i) one whose defect region is a V region in its entire plane, (ii) one including the V region, an OSF region, and an N region, and (iii) one whose defect region is the N region in its entire plane were prepared, and they were subjected to chamfering, lapping/surface grinding/double head grinding, and etching in accordance with a conventional method.

Example 1

Figure 4:
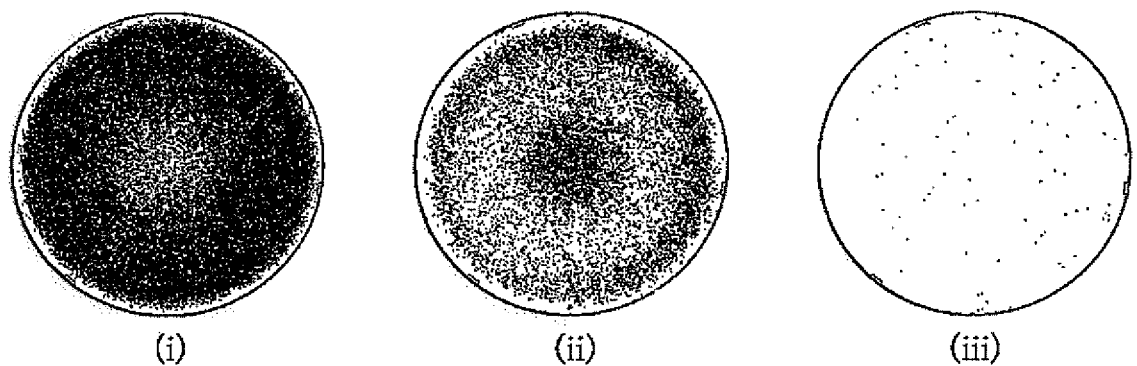
FIG. 4 is wafer maps showing defect density distributions of wafers (i) to (iii) measured in Example 1.

Mirror-surface processing was performed by polishing and cleaning to the thus prepared silicon wafers (i) to (iii) in accordance with the conventional method. Then, a haze level of a mirror-surface-processed surface of each wafer was measured in a DWO mode (a laser wavelength: 266 nm) of SurfScan SP3 manufactured by KLA-Tencor Corporation, and it was confirmed that all the wafers had the haze levels of 0.055 to 0.060 ppm. Subsequently, the number of defects and a defect density distribution on the mirror-surface-processed surface of each wafer were measured by using SurfScan SP5 which can measure defects having a size of 15 nm or less and is manufactured by KLA-Tencor Corporation. FIG. 4 shows defect density distributions (wafer maps) of the respective wafers from which defects of 14 nm or more were detected. It is to be noted that the number of the defects was approximately 60,000 in the wafer (i), approximately 10,000 in the wafer (ii), and approximately 200 in the wafer (iii).

First, comparing the number of the defects alone, the wafer (i), the wafer (ii), and the wafer (iii) have considerable differences in the number of the defects, and these wafers were able to be discriminated from each other. Then, comparing the defect density distributions, grown-in defects were revealed on the entire wafer surface of the wafer (i), a ring-like defect (OSF ring) near an outer periphery and defects considered to be caused by the V region in a central portion were revealed in the wafer (ii), the entire wafer surface had less defects in the wafer (iii), and hence these wafers were able to be discriminated from each other. Based on these results, the defect region of the silicon wafer (i) was determined as the V region in its entire plane, the silicon wafer (ii) was determined as one including the V region, the OSF region, and the N region, and the defect region of the silicon wafer (iii) was determined as the N region in its entire plane.

Furthermore, defect regions were determined based on the number of the defects and the defect density distribution of each of the wafers (i) to (iii) measured as described above, a correspondence table (not shown) of the defect regions, and the number of the defects and the defect density distribution on the silicon wafer surface of the silicon single crystal having the initial oxygen concentration of 11 ppma obtained in advance. Thereby, it was able to determine that the defect region of the silicon wafer (i) was the V region in its entire plane, the defect region of the silicon wafer (ii) included the V region, the OSF region, and the N region, and the defect region of the silicon wafer (iii) was the N region in its entire plane.

Comparative Example 1

Figure 5:
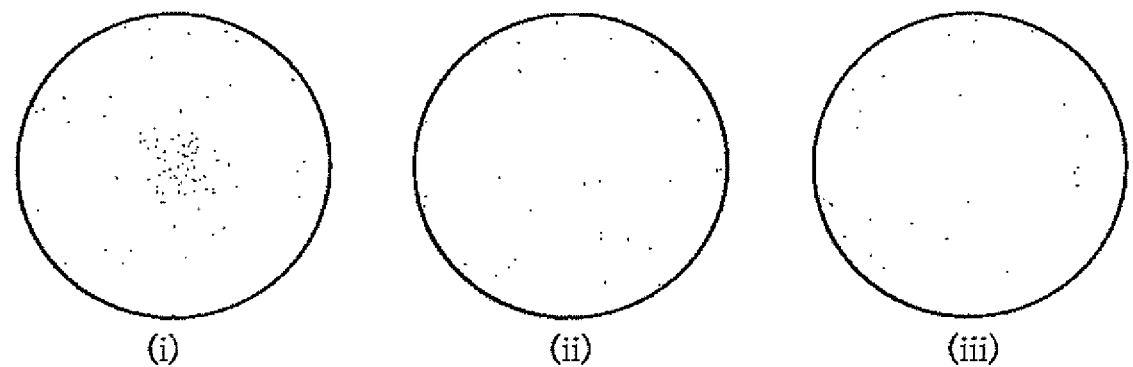
FIG. 5 is wafer maps showing defect density distributions of wafers (i) to (iii) measured in Comparative Example 1.

The number of defects and a defect density distribution of each mirror-surface-processed silicon wafer, which had been subjected to the measurement of the number of the defects and the defect density distribution in Example 1, were measured by using the DWO mode of SurfScan SP3 manufactured by KLA-Tencor Corporation which can measure defects having a size of not less than 20 nm. FIG. 5 shows the defect density distributions (wafer maps) obtained from detection of defects which are 26 nm or more. It is to be noted that, as the number of the defects, a wafer (i) had approximately 200 defects, a wafer (ii) had approximately 40 defects, and a wafer (iii) had approximately 40 defects.

First, comparing the numbers of the defects alone, the number of the defects of the wafer (i) is higher than those of the wafer (ii) and the wafer (iii), but the number of the defects of the wafer (ii) is substantially equal to that of the wafer (iii), and hence the wafer (ii) and the wafer (iii) were not able to be discriminated from each other. Then, comparing the defect density distributions, as shown in FIG. 5, the wafer (i) has more defects in a wafer central portion thereof than the wafer (ii) and the wafer (iii), but the wafer (ii) and the wafer (iii) have less defects on their entire wafer planes, and hence the wafer (ii) and the wafer (iii) were not able to be discriminated from each other. As described above, it can be understood that, when the particle counter having a defect detection capability of 20 nm level (namely, it cannot measure defects having a size of 15 nm or less) is used, defect regions cannot be determined even though the haze level after the mirror-surface processing is set to 0.06 ppm or less.

Comparative Example 2

Figure 6:
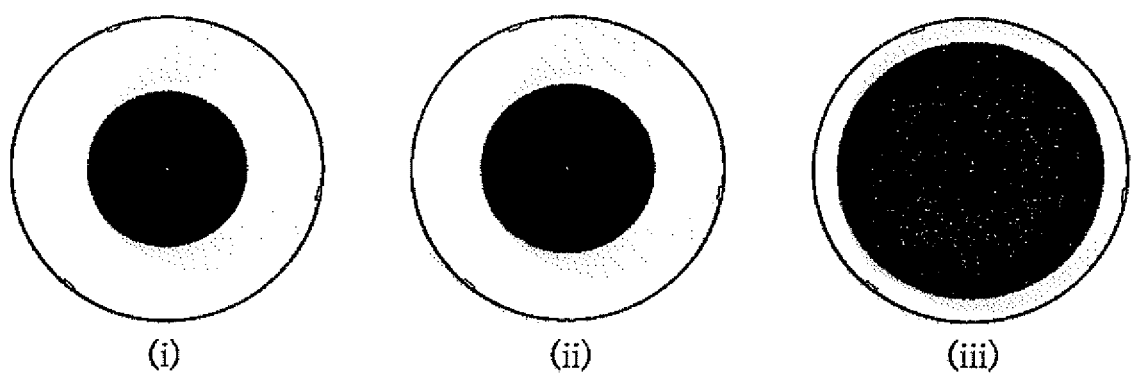
FIG. 6 is wafer maps showing defect density distributions of wafers (i) to (iii) measured in Comparative Example 2.

Silicon wafers (i) to (iii) were prepared like Example 1, the mirror-surface processing was performed under changed polishing conditions, and it was confirmed that mirror-surface-processed wafer surfaces of all the wafers had haze levels of 0.068 to 0.72 ppm, respectively. Then, the numbers of defects and defect density distributions on the mirror-surface-processed wafer surfaces were measured by using SurfScan SP5 manufactured by KLA-Tencor Corporation which can measure defects having a size of 15 nm or less. FIG. 6 shows the defect density distributions (wafer maps) obtained from detection of the defects of 14 nm or more. It is to be noted that the numbers of the defects of all the wafers overflowed in the particle counter, and the measurement of the numbers of the defects failed.

The numbers of the defects of all the wafers overflowed in the particle counter as described above, accurate defect density distributions were not obtained as shown in FIG. 6, and hence the wafers (i) to (iii) were not able to be discriminated from each other. That is because a reduction in haze components after the mirror-surface processing was insufficient, and hence both defect components and the haze components on each silicon wafer surface were detected as defects by the particle counter. Thus, it can be understood that, when the haze level after the mirror-surface processing exceeds 0.06 ppm, defect regions cannot be determined even though the particle counter having a defect detection capability of 10 nm level (namely, it can measure defects having a size of 15 nm or less) is used.

Thus, it has been revealed that crystal defects can be sensitively detected and defect regions of each silicon wafer can be determined from the measured number of defects and/or defect density distribution in a short time by a nondestructive inspection by setting a haze level of each silicon wafer which is to be subjected to the defect region determination to a predetermine value or less and by using a particle counter with a predetermined detection accuracy.

It is to be noted that the present invention is not restricted to the embodiment. The embodiment is an illustrative example, and any example which has substantially the same structure and exerts the same functions and effects as the technical concept described in claims of the present invention is included in the technical scope of the present invention.

The invention claimed is:

1. A method for determining a defect region of a silicon wafer which is sliced off from a silicon single crystal manufactured by a CZ method, comprising:
   (1) mirror-surface processing the silicon wafer in such a manner that a haze level of a surface thereof in haze measurement performed by a particle counter which uses a laser having a wavelength of 266 nm becomes 0.06 ppm or less;
   (2) measuring one or both of the number of defects and a defect density distribution on the mirror-surface-processed surface of the silicon wafer by using a particle counter capable of measuring defects having a size of 15 nm or less; and
   (3) determining the defect region of the silicon wafer from one or both of the measured number of the defects and defect density distribution.

2. The method for determining a defect region according to claim 1, wherein a V region, an OSF region, and an N region are determined as the defect region.

3. The method for determining a defect region according to claim 1, wherein, before (3) by the particle counter used in (2), one or both of the number of defects and a defect density distribution on a surface of a silicon wafer which has the same oxygen concentration as that of the silicon wafer and has an already identified defect region are measured and a correspondence relation between the defect region and one or both of the number of the defects and the defect density distribution on the surface of the silicon wafer is obtained in advance, and,
   in (3), the defect region of the silicon wafer is determined from one or both of the number of defects and the defect density distribution measured in (2) based on the correspondence relation obtained in advance.

4. The method for determining a defect region according to claim 2, wherein, before (3) by the particle counter used in (2), one or both of the number of defects and a defect density distribution on a surface of a silicon wafer which has the same oxygen concentration as that of the silicon wafer and has an already identified defect region are measured and a correspondence relation between the defect region and one or both of the number of the defects and the defect density distribution on the surface of the silicon wafer is obtained in advance, and,
   in (3), the defect region of the silicon wafer is determined from one or both of the number of defects and the defect density distribution measured in (2) based on the correspondence relation obtained in advance.

5. The method for determining a defect region according to claim 1, wherein the silicon wafer has oxygen concentration of 5 to 20 ppma (JEIDA).

6. The method for determining a defect region according to claim 2, wherein the silicon wafer has oxygen concentration of 5 to 20 ppma (JEIDA).

7. The method for determining a defect region according to claim 3, wherein the silicon wafer has oxygen concentration of 5 to 20 ppma (JEIDA).

8. The method for determining a defect region according to claim 4, wherein the silicon wafer has oxygen concentration of 5 to 20 ppma (JEIDA).

* * * * *